United States Patent
Morales et al.

(10) Patent No.: US 9,649,180 B2
(45) Date of Patent: May 16, 2017

(54) MONOLITHIC SUPPORT STRUCTURE FOR USE IN IMPLANT-SUPPORTED DENTAL DEVICES AND METHODS OF MAKING THE SAME

(71) Applicant: James R. Glidewell Dental Ceramics, Inc., Newport Beach, CA (US)

(72) Inventors: David Morales, Oceanside, CA (US); Nhung Tieu Truong, Anaheim, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 100 days.

(21) Appl. No.: 14/709,752

(22) Filed: May 12, 2015

(65) Prior Publication Data

US 2016/0331494 A1    Nov. 17, 2016

(51) Int. Cl.
A61C 13/00    (2006.01)
A61C 13/01    (2006.01)
A61C 13/08    (2006.01)
A61C 13/083    (2006.01)

(52) U.S. Cl.
CPC .......... A61C 13/01 (2013.01); A61C 13/0004 (2013.01); A61C 13/0022 (2013.01); A61C 13/082 (2013.01); A61C 13/083 (2013.01)

(58) Field of Classification Search
CPC ... A61C 13/0004; A61C 13/01; A61C 13/082; A61C 13/0022; A61C 13/083
See application file for complete search history.

(56) References Cited

U.S. PATENT DOCUMENTS

| | | | |
|---|---|---|---|
| 2,293,909 A | 8/1942 | Lee et al. | |
| 6,322,728 B1 | 11/2001 | Brodkin et al. | |
| 6,361,318 B1* | 3/2002 | Back | A61C 13/0004 433/173 |
| 6,692,254 B1 | 2/2004 | Kligerman et al. | |
| 6,814,575 B2* | 11/2004 | Poirier | A61C 1/084 433/75 |
| 7,208,037 B2 | 4/2007 | Binder et al. | |
| 8,100,692 B2 | 1/2012 | Diangelo et al. | |
| 8,298,329 B2 | 10/2012 | Knapp et al. | |
| 9,358,083 B2* | 6/2016 | Clausen | A61C 13/0004 |
| 2003/0183964 A1 | 10/2003 | Daskalon et al. | |

(Continued)

FOREIGN PATENT DOCUMENTS

| | | | |
|---|---|---|---|
| WO | WO2010139031 A2 | 12/2010 | |
| WO | WO2014056606 A2 | 4/2014 | |
| WO | WO2015031062 A1 | 3/2015 | |

*Primary Examiner* — Glenn Richman
(74) *Attorney, Agent, or Firm* — Dianne Burkhard

(57) ABSTRACT

A dental device is described that comprises a monolithic support structure for use in implant-supported dental restoration applications for partially or fully edentulous patients. The monolithic support structure comprises a unitary support body with one or more teeth projections projecting from the support body, and at least one support region providing a framework for integrating discrete artificial teeth adjacent the teeth projections. An implant-supported dental device is also provided that comprises the monolithic support structure, one or more artificial teeth, and a gingival region comprised of a formable material that secures artificial teeth within the framework of the monolithic support structure.

14 Claims, 4 Drawing Sheets

(56) References Cited

U.S. PATENT DOCUMENTS

| | | |
|---|---|---|
| 2006/0105294 A1 | 5/2006 | Burger et al. |
| 2007/0154864 A1 | 7/2007 | Deer et al. |
| 2008/0131846 A1 | 6/2008 | Marshall et al. |
| 2009/0115084 A1 | 5/2009 | Moon |
| 2009/0142733 A1 | 6/2009 | Marshall et al. |
| 2012/0308837 A1 | 12/2012 | Schlechtriemen et al. |
| 2013/0101962 A1 | 4/2013 | Howe |
| 2013/0231239 A1 | 9/2013 | Carden |
| 2013/0252203 A1 | 9/2013 | Clunet-Coste et al. |
| 2013/0313738 A1 | 11/2013 | Carden |
| 2014/0000314 A1* | 1/2014 | Ritzberger ........... A61K 6/0215 65/33.1 |
| 2014/0101869 A1 | 4/2014 | Carden et al. |
| 2014/0109797 A1 | 4/2014 | Carden |
| 2014/0255873 A1 | 9/2014 | Bullis et al. |
| 2015/0182314 A1 | 7/2015 | Morales et al. |
| 2015/0182316 A1 | 7/2015 | Morales et al. |

* cited by examiner

MONOLITHIC SUPPORT STRUCTURE FOR USE IN IMPLANT-SUPPORTED DENTAL DEVICES AND METHODS OF MAKING THE SAME

BACKGROUND

The manufacturing of implant-supported dental restorations often include a complex series of design steps requiring multiple patient-dentist visits, and interactions with a manufacturing dental laboratory before completion of a final dental device. Implant-supported dentures may include a metal support bar that supports denture teeth and acrylic gingiva, and attaches to patient implants. Design and manufacture of the support bar further complicates the denture making process.

Metal bars used to connect a denture to implants may stabilize and strengthen the device to avoid breakage. However, fitting a denture onto the bar can be difficult and often imprecise. Further, it may be difficult to preserve the registration of the bar and the try-in denture during removal from a plaster model, try-in stage and/or transportation of the devices between the dentist and laboratory.

U.S. Pat. No. 6,692,254 described an apparatus and method for fastening a denture plate with artificial teeth to a plurality of implants screwed into the bone. A rigid metal bar is prepared that registers with implants and is affixed to a denture plate. Screws passing through holes in the bar attach the bar and denture plate to implants are described as distributing tooth forces among implants. US2013/0252203 describes a dental bridge armature designed to be screw-fastened onto dental implants and includes reinforcing elements formed by long fibres pre-impregnated with resin. The armature is then included in a PMMA coating by a pressing or injection technique.

Commonly owned US 2014/0255873, which is hereby incorporated by reference in its entirety describes an implant-supported denture device made from a material that may not require a separate substructure. It may comprise a monolithic component, with gingival and teeth regions, that attaches directly to implants. A ceramic monolithic component having all ceramic teeth and gingiva lacks acrylic avoiding breakage that may occur in traditional dentures.

SUMMARY

A dental device is described that comprises a monolithic support structure for use in implant-supported dental restoration applications for partially or fully edentulous patients having dental implants. The monolithic support structure comprises a unitary support body with one or more teeth projections projecting from the support body, and at least one support region that provide a framework for integrating discrete artificial teeth within areas adjacent the teeth projections.

An implant-supported dental device is also provided that comprises the monolithic support structure, one or more artificial teeth that are discrete from and adjacent the teeth projections of the monolithic support structure. A gingival region comprised of a formable material may secure artificial teeth within the framework of the monolithic support structure. In one embodiment, a formable material also encapsulates the support body of the monolithic support structure and the cervical regions of the teeth projections. The monolithic support structure further comprises apertures that register with a patient's implants for attachment of the implant-supported dental device to the patient's jaw.

Implant-supported dental devices and corresponding monolithic support structures may be designed for both partially or completely edentulous patients, and for one or both ridges. Moreover, the dental device may comprise a bridge for a partially edentulous patient.

An implant-supported dental device may be digitally designed based on information collected from a patient regarding their oral anatomy and positional geometry of the implant. Patient scan data or images may be used to design a monolithic support structure. The digital design comprises a digital support body with a contour corresponding to the arch form of a patient and natural and/or artificial teeth location. Apertures are designed in registration with patient implants based on geometric positional information regarding the implant. A digital teeth design may be made for compatibility with any remaining dentition of the patient, and/or with a selected dental design based on dentist input. Several digital teeth may be selected for integration with the digital support structure forming the teeth projections of the monolithic support structure. Upon formation of a digital design and manufacturing instructions, the monolithic structure may be milled from a single body of porous ceramic material and sintered into a densified monolithic support structure. Artificial teeth are aligned in one or more support regions formed between teeth projections. Acrylic may be used to encapsulate the support body and cervical regions of the teeth projections, and to secure artificial teeth in place and provide an artificial gingiva. Artificial teeth may comprise a material with a lower flexural strength or fracture toughness than the material of the monolithic support. Therefore, in the implant-supported device, teeth projections of the monolithic support structure may protect artificial teeth from, for example, chewing or biting forces.

BRIEF DESCRIPTION OF THE DRAWINGS

A more complete understanding of the present invention may be derived by referring to the detailed description and claims when considered in connection with the Figures.

DETAILED DESCRIPTION

Figure 1A:
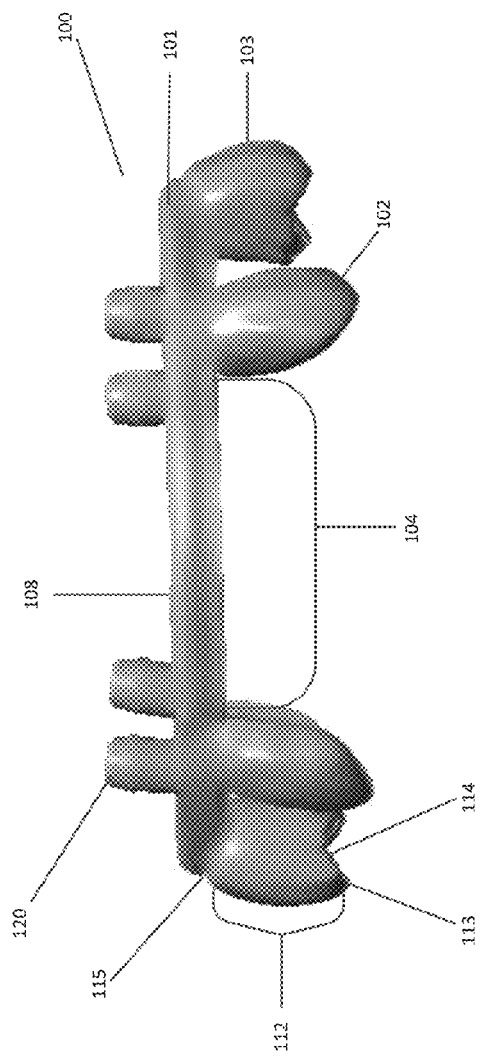
FIG. 1A is a front planar view of an exemplary embodiment of a monolithic support structure.

With reference to FIG. 1A, a monolithic support structure (100) is provided. The monolithic support structure (100) may be incorporated into an implant-supported dental device (200), exemplified in FIG. 2, that attaches to implants in an edentulous portion of a patient's oral anatomy.

The exemplary monolithic support structure (100) illustrated in FIGS. 1A-1E, comprises a support body (101), one or more teeth projections (102 and 103) that project from the support body (101), and at least one artificial tooth support region (104, 105) adjacent the teeth projections. One or more apertures (106, 107) extending through the thickness of the monolithic support structure may be located through the support body (101), through one or more teeth projections (102), or partially through a tooth projection and partially through the support body. Attachment means, such as screws, extend through the apertures for attachment of an implant-supported dental device to patient implants.

The monolithic support structure has an attachment side (108) oriented toward a patient's edentulous ridge, and a crown side (109) that is opposite the attachment side (108). A lingual side (110) is proximate a patient's tongue, and a buccal side (111) is closest the inner surface of a patient's cheek. The support body has a width dimension extending from lingual side to buccal side that may be smaller than the width of the patient's ridge. The contour of the support body (101) generally corresponds to the arch form of the portion of the edentulous jaw for which the restoration is designed.

One or more teeth projections (102, 103) are monolithic continuations of the support body (101). Each tooth projection may represent a single restoration tooth, replacing a single natural tooth, and having an anatomical crown region (112) fully contoured with complete anatomical features on facial (buccal or labial), lingual and/or incisal/occlusal surfaces. Anatomical features on the tooth projections may include cusps (113), ridges, fossa, grooves (114), and the like. The crown region of each tooth projection may be discrete from other teeth projections. Optionally, a single projection may replace two or more adjacent natural teeth, and comprise a crown region with anatomical features consistent with each tooth type. The one or more teeth projections may comprise a cervical region (115) located between the crown region (112) and the support body (101), that is subgingivally located in the implant-supported dental device.

In the implant-supported dental device (200), the crown region (112, 201, and 201') of the teeth projections (102, 103) of the monolithic support structure is generally exposed and extends beyond the artificial gingiva (202). The monolithic support structure (100), designed from patient-specific data, comprises teeth projections (102, 103) that have size, shape and anatomical features that are compatible with existing natural dentition or artificial dentition of the patient, and that require minimal finishing beyond optional staining, and/or glazing prior to making the implant-supported dental device.

The number of teeth projections (102, 103) may vary depending on the final implant-supported dental device. For example, the number of teeth projections on the monolithic support structure may comprise one, two, three, four, five, six, seven or eight teeth projections. In the exemplary embodiment of FIG. 1C, anterior teeth projections (102, 102') located in the anterior region (116) of the monolithic support structure may correspond to one or more of cuspids (canines), central incisors and lateral incisors, as found in natural or artificial dentition. Posterior teeth projections (103, 103') generally located in the posterior region (117) may correspond to one or more of first bicuspids (first premolar), second bicuspids (second premolar), first molar, and second molar.

The monolithic support structure comprises support regions in which artificial teeth are aligned in the implant-supported dental device. The support regions may comprise one or more anterior support regions, posterior support regions, or a support regions spanning both anterior and posterior regions of the structure. In one embodiment exemplified in FIGS. 1A-1E, a monolithic support structure designed to restore a full-arch comprises an anterior region (116) and two posterior regions (117, 117'), each of which comprising a support region for supporting artificial teeth. In one alternate embodiment of a monolithic support structure designed to restore only a portion of a patient's arch, a single support region may be provided. In a further embodiment, a monolithic support structure is designed accommodate both anterior and posterior artificial teeth within one support region that is between an anterior tooth projection (such as a central or lateral incisor) and a posterior tooth projection (such as a molar).

In one embodiment, a monolithic support structure comprising anterior and posterior regions may comprise only posterior teeth projections, or only anterior teeth projections. In one specific example, a full arch restoration may comprise two posterior teeth projections (e.g., a first bicuspid and a first molar) on each side of the monolithic support structure, and an anterior support region with no teeth projections between the two first bicuspid teeth projections of each posterior region.

Upper and lower opposing monolithic support structures may comprise opposing teeth projections designed in occlusal relationship. In one exemplary embodiment, upper and lower full-arch implant-supported dental devices comprising four pairs of opposing teeth projections are designed for occlusal contact. In this embodiment, the upper arch may comprise two anterior teeth projections such as two cuspid teeth projections, and two posterior teeth projections, such as two molar teeth projections, that are in occlusion with the teeth projections of the lower arch.

A partial implant-supported dental device may comprise about 2 to about 12 restoration teeth, including at least one tooth projection and at least one artificial tooth. In one specific embodiment, a quadrant monolithic support structure designed for a right or left side of an edentulous arch may comprise at least one anterior tooth projection, at least one posterior tooth projection, and one or more artificial teeth support regions for positioning artificial teeth.

At least one aperture (106, 107) extending through the thickness of the monolithic support structure is in registration with a patient's implants. As seen in FIGS. 1C, 1D and 1E, at least one aperture (106, 107) may extend through the support body in an anterior region, a posterior region, or may extend through one or more teeth projections. In some restorations, a patient's implant placement in an anterior region requires an aperture to be located through an anterior restoration tooth of an implant-supported dental device, disadvantageously requiring a reduction of an artificial denture tooth to accommodate the aperture. In this embodiment, one or more teeth projections may be advantageously designed as the restoration tooth (teeth) so that the aperture passes through the sturdy tooth projection instead of an artificial denture tooth, thus, eliminating the need to modify an artificial denture tooth to accommodate the aperture.

The support body may optionally comprise at least one aperture flange region (119), or at least one guide cylinder (120) encircling the aperture, or both. The aperture flange region and/or guide cylinder may also be a unitary, monolithic projection from the support body comprising the same material as the monolithic support structure. To minimize the overall buccal-to-lingual dimension, or width, of the support body, the aperture flange region (119) surrounds an aperture, where placement of the aperture extends beyond the predominant width dimension and contour of the support body.

Figure 1B:
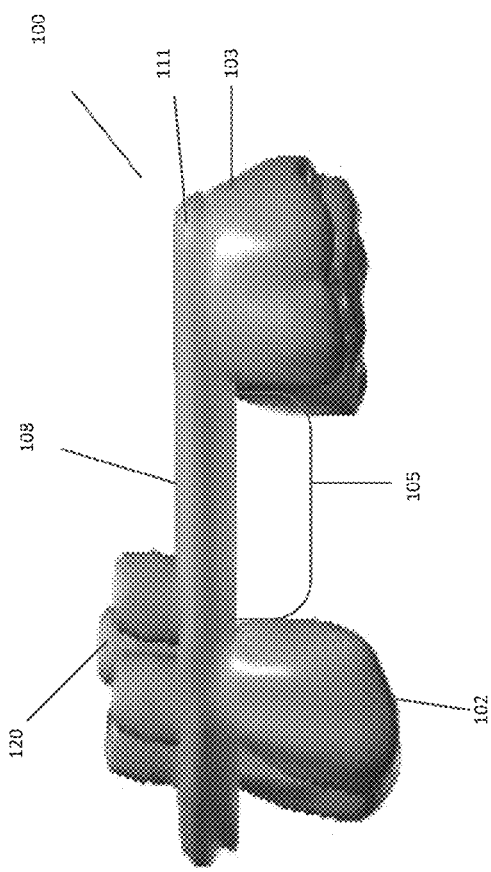
FIG. 1B is a side-view of an exemplary embodiment of a monolithic support structure.
Figure 1C:
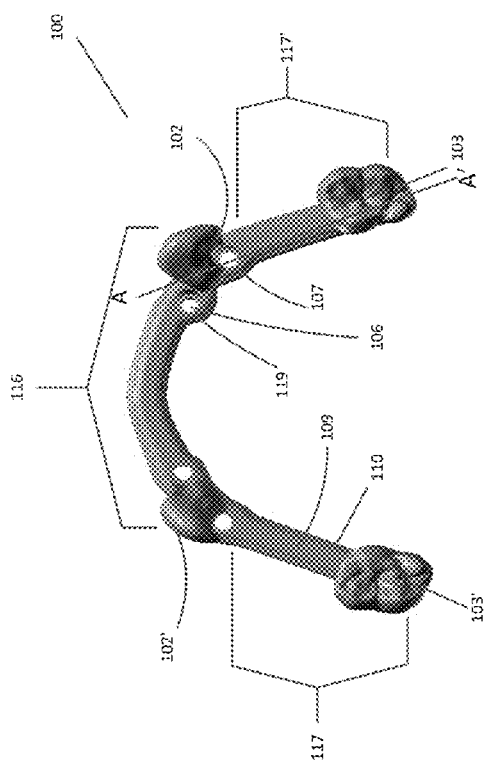
FIG. 1C is a top view of the crown side of an exemplary embodiment of a monolithic support structure.
Figure 1D:
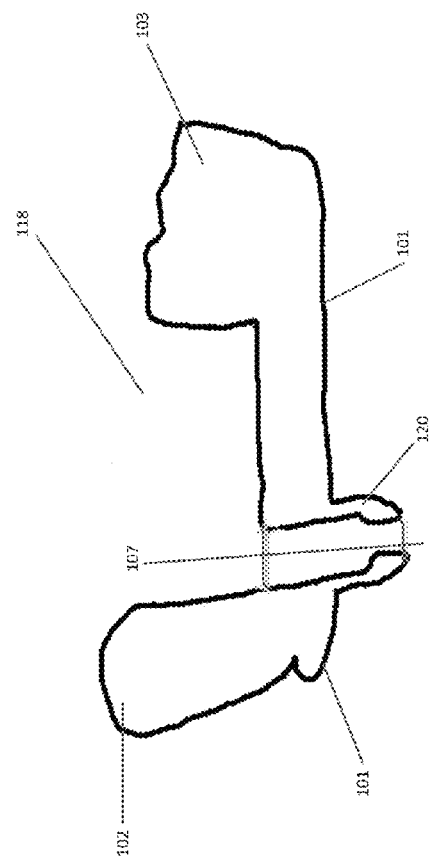
FIG. 1D is a cross-sectional representation of the monolithic support structure of FIG. 1C.
Figure 1E:
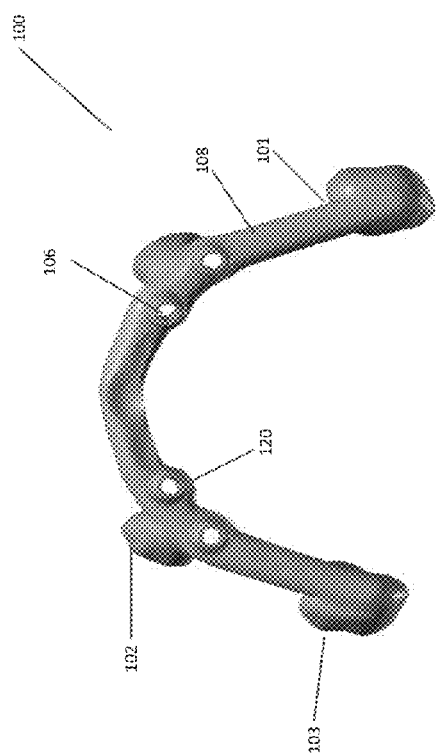
FIG. 1E is a top view of the attachment side of an exemplary embodiment of a monolithic support structure.

The guide cylinder (120) comprises a hollow cylindrical projection on the attachment surface of the support body, as exemplified in FIGS. 1A, 1B, and 1D. The geometry of the guide cylinder (120) is designed based on the positional orientation of the implant having a geometry and orientation matching the implant. An attachment means, such as a screw having a geometry and size compatible with the patient's implant, is inserted into the aperture on the crown side, passing through the support body, and optional guide cylinder, to attach the final implant-supported dental device to the patient's implants.

Optionally, an insert, such as an implant-compatible non-engaging abutment insert that is compatible with the implant system of the patient, may be placed within the guide cylinder and may abut the implant upon attachment of the implant-supported dental device. The insert may be comprised of a metal, such as titanium. In one embodiment, an insert (205), may be secured in the implant-supported device by the formable material (202) that encapsulates the monolithic support structure. Optionally, an insert comprises an insert flange (206) having a diameter larger than the guide cylinder to maintain the insert position within the guide cylinder. An attachment means, such as a screw that is compatible with the insert and implant system, passes through the insert within the guide cylinder, connecting to the implant for attachment of the implant-supported dental device.

As exemplified in FIG. 1D, the support body (101), the one or more teeth projections (102, 103), and optional guide cylinders (120), form a unitary, monolithic support structure. By unitary is meant that the monolithic support structure is constructed as one piece. FIG. 1D illustrates a representative cross-section (118) (shown as line A-A' in FIG. 1C) taken through a portion of a monolithic support structure through teeth projections (102, 103), aperture (107), guide cylinder (120), and support body (101) showing a continuous material that extends through the shaped body from the attachment side to the occlusal surface of the tooth projection.

Processes for manufacturing the monolithic support structure may include, but are not limited to automated manufacturing processes, such as an additive or subtractive processes, injection molding, or casting. Rapid manufacturing processes, including subtractive or additive manufacturing processes may be used. Subtractive manufacturing processes include, carving, grinding or milling, or CNC milling or machining processes, wherein the monolithic support structure is made from a single piece of material, such as a single ceramic monolithic block. For example, a 5-axis Haas milling machine (Hass Automation) may be used to form a monolithic support structure from a single ceramic block of material. Additive manufacturing processes may also be used to form a monolithic support structure, including technologies such as 3D printing technologies, stereo lithography, selective laser sintering (SLS), and fused deposition modeling.

The monolithic support structure may be made from a hard, durable material, or a material having mechanical properties such as high flexural strength, wear resistance, and/or fracture toughness such as a ceramic material. Optionally, the monolithic support structure is substantially free of metal, and optionally, the monolithic support structure is substantially free of titanium.

Ceramic materials include dental ceramics suitable for use in dental restorations, including zirconia, alumina, titanium dioxide, and mixtures thereof. Zirconia ceramic materials may comprise zirconia, stabilized zirconia, such as tetragonal stabilized zirconia, and mixtures thereof. Stabilized zirconia may include yttria-stabilized zirconia, such as those materials commercially available from Tosoh USA, that are suitable for use dental restoration applications. Yttria-stabilized zirconia may comprise about 3 mol % to about 5 mol % yttria, or about 2 mol % to about 7 mol % yttria. Suitable ceramic powders may also comprise zirconia stabilized with about 3%, 5% or 7% by mass yttria, such as 3Y-TZP available through Tosoh.

Ceramic powders made of the above formulations may be processed into ceramic forms suitable for use in making dental restorations by known methods. Ceramic powders may be pressed, for example, by biaxial or iso-static pressing, into millable forms, and the ceramic powders may optionally comprise binders and processing aids to facilitate block formation. Optionally, ceramic powder may be processed by slip casting processes including, but not limited to, processes described in U.S. Patent Publication Nos. 2009/0115084; 2013/0231239; and 2013/0313738; and U.S. Pat. No. 8,298,329, all of which are incorporated by reference in their entirety. Ceramic forms, such as yttria-stabilized tetragonal zirconia sold as blocks, discs, or blanks, having a size and shape suitable for making a full or partial arch monolithic structure, and sold under the trade name BRUXZIR (Glidewell Laboratories) may be suitable for use herein.

In one embodiment, the monolithic support structure is shaped as a porous body from a green-state or partially sintered ceramic block. In one embodiment, green-state material is partially sintered to a bisque-state that is sufficiently hard to retain its structure during grinding or milling into a monolithic support structure design, and soft enough to allow rapid shaping by a milling tool. CAD/CAM milling processes may be used to shape the monolithic support structure according to milling instructions based on a digital design. The porous or partially sintered body is then sintered at high temperature. Bisque stage ceramic materials include ceramic materials that have been partially densified or heated for example, to remove water or binder, while retaining some porosity and having a density below the maximum theoretical density of the material. In some embodiments, bisque stage ceramics are formed by heating green ceramic materials at a temperature in the range of about 850° C. to about 1200° C. for about 1 to 2 hours, or until a desired density is achieved. In some embodiments green ceramic materials fabricated from yttria-stabilized tetragonal zirconia polycrystals doped with alumina (BruxZir® zirconia, Glidewell Dental Laboratories) may be heated at a temperature in the range of about 1020° C. to about 1050° C., for about 24 hours to about 60 hours to form bisque ceramic materials having a density in the range of about 3.15 to about 3.35 g/cm$^3$. Bisque stage ceramics include materials having a density that is approximately 50% to about 90% of the maximum theoretical density of the ceramic material. Zirconia-containing bisque stage ceramics include those that have a density of about 3.1 to about 3.4 g/cm$^3$, and which can be densified to a density greater than or equal to about 6 g/cm$^3$. In some embodiments, a bisque stage ceramic material comprises yttria-stabilized tetragonal zirconia and has a density in the range of about 6.01 g/cm$^3$ to about 6.1 g/cm$^3$ after sintering at a temperature in the range of from about 1350° C. to about 1600° C.

Green-state or partially sintered ceramic blocks having known shrinkage rates can be fabricated in CAD/CAM systems by designing the monolithic support structure to a dimension larger than the final sintered structure by a scaled factor that anticipates a highly predictable reduction in size upon sintering to full density. A subsequently sintered monolithic support structure having reduced in size from the bisque stage structure conforms to the patient-specific design.

Advantageously, sintered yttria-stabilized zirconia materials suitable for use herein may comprise high light transmission in about the 500-800 nm wavelength range. Moreover, sintered ceramic materials for use in making monolithic support structures have high wear resistance, fracture toughness, and high flexural strength when tested by a flexural strength test method for zirconia materials according to the methods outlined in ISO 6872:2008, measured and calculated according to the 3 point flexural strength test described for Dentistry—Ceramic Materials. For example, ceramic materials used herein may have a flexural strength value greater than about 650 MPa, or greater than about 800 MPa, when tested according to the above test method.

The ceramic blocks may be shaded to achieve the color of natural or artificial dentition. Coloring agents may be incorporated during block formation to produce a shaded monolithic support structure having teeth projections that match the shade of natural dentition or artificial teeth without further colorization. U.S. Patent Publication No. 2013/0231239, incorporated by reference herein, in its entirety, describes methods for coloring ceramics by colloidal dispersion and casting the ceramics by slip casting methods. A further example includes commonly owned, U.S. Patent Publication No. 2014/0109797, which teaches methods for making colored ceramic powder, formed into green state ceramic bodies by press manufacturing processes, is also incorporated by reference herein in its entirety. Alternatively, or additionally, after milling or grinding, monolithic structures may be colorized and/or glazed in the bisque or sintered state, for example, by methods known in the dental industry, or by processes described in commonly owned U.S. Patent Publication No. 2014/0101869, which is hereby incorporated by reference in its entirety.

The crown regions of teeth projections may be shaded or colorized to match the shade of a selected artificial tooth which will be used in the implant-supported dental device, or to match the shade of any surrounding or opposing natural dentition. The support body may be shaded or colorized a pink or flesh-tone shade to reduce visibility of the monolithic support structure through the formable material in which it is encapsulated. Ceramic powders, ceramic materials, or the monolithic support structure, may be shaded or colorized to match a commercially available artificial tooth, for example, in a Bioform shade (Dentsply International Inc.) or VITA shade (such as Vita Classic Shade A1, A2, A3, etc., Vita Zahnfabrik).

Figure 2:
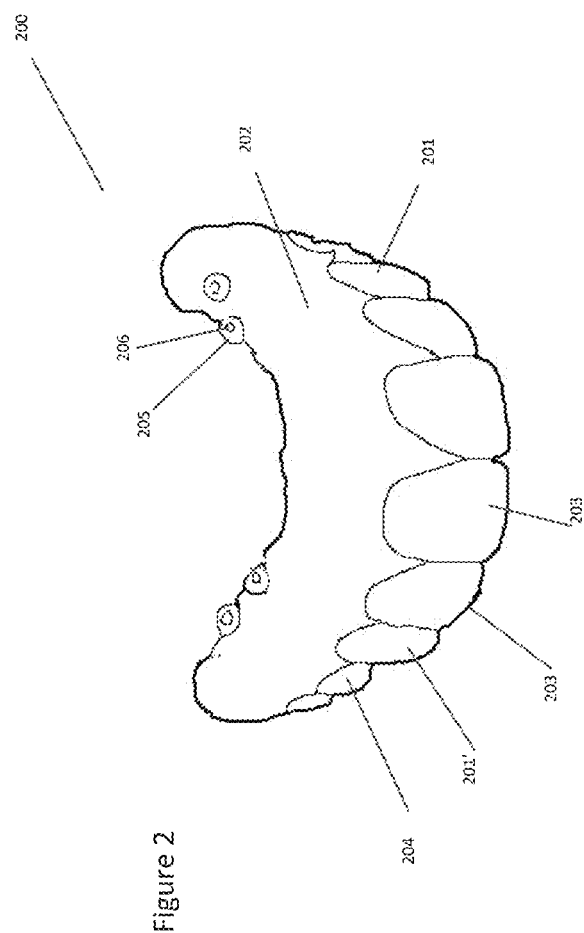
FIG. 2 is a front planar view of an exemplary embodiment of an implant-supported dental device comprising a monolithic support structure.

An implant-supported dental device (200), exemplified in FIG. 2, is a composite of the monolithic support structure, artificial teeth, and optionally, artificial gingiva. The monolithic support structure provides a framework for integrating discrete artificial teeth (203, 204), such as commercially available denture teeth, and artificial gingiva (202) to form the implant-supported dental device.

Figure 3A:
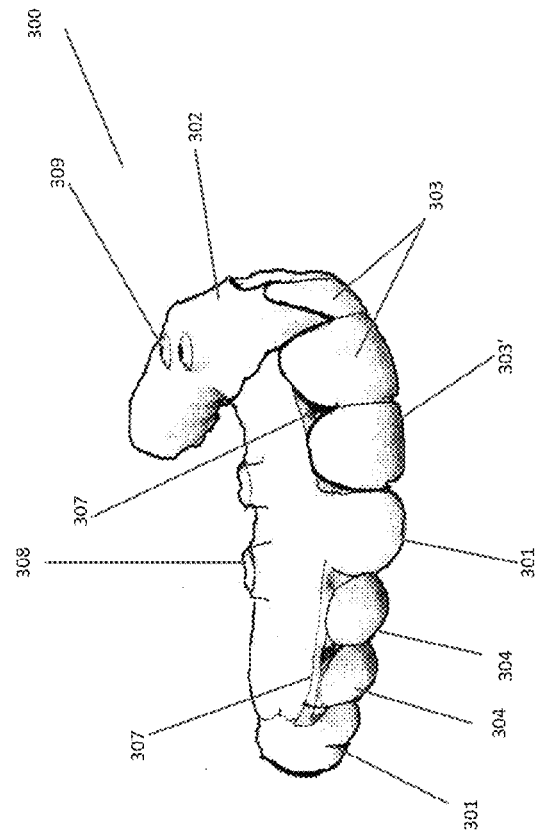
FIG. 3A is a side buccal view of an exemplary embodiment of an implant-supported dental device which has been altered for illustrative purposes.
Figure 3B:
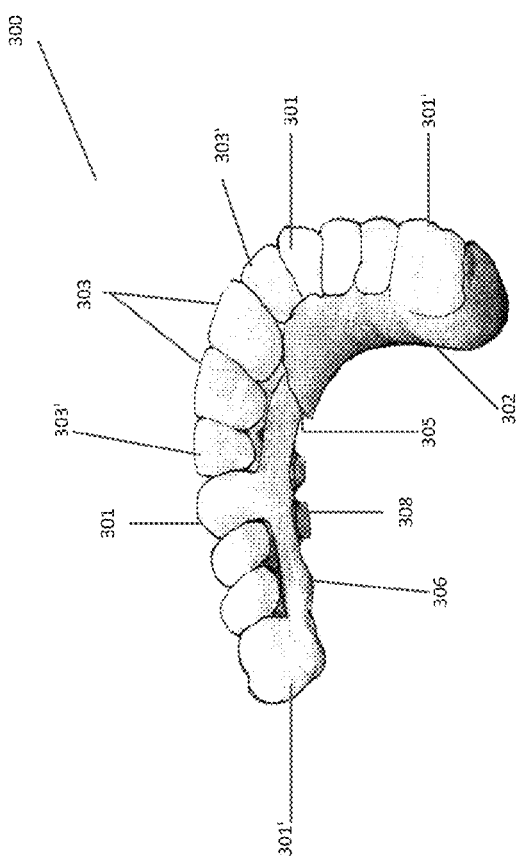
FIG. 3B is a side, lingual view of an exemplary embodiment of an implant-supported dental device which has been altered for illustrative purposes.

FIGS. 3A and 3B depicts an exemplary implant-supported dental device (300) in which a portion of the artificial gingiva (302) has been removed, for illustrative purposes only, to show alignment of artificial teeth (303, 304) in anterior and posterior artificial tooth support regions (305, 306) between teeth projections (301, 301') and adjacent the support body (307) of the monolithic support structure. The monolithic support structure comprises two anterior teeth projections (cuspids) (301), two posterior teeth projections (molars) (301'), and guide cylinders (308) surrounding apertures.

Shown in the embodiment of FIGS. 3A and 3B, discrete artificial teeth comprise two central incisors (303) and two lateral incisors (303'), in the anterior region, and in posterior regions, comprise bicuspids ($1^{st}$ and $2^{nd}$) (304). Placement of teeth projections in both anterior and posterior regions of the monolithic support structure may balance and distribute contact between anterior and posterior teeth projections maintaining vertical dimension of the upper and lower jaw, and protecting the artificial teeth from wearing away.

In FIGS. 3A and 3B, the guide cylinders (308) comprise metal inserts (309) that guide an attachment means, such as a screw, for attaching the implant-supported dental device to a patient's implants.

An artificial gingiva (202, 302) may be formed from a formable material, in surrounding relationship to the support body and the cervical region of the teeth projections. The formable material may comprise an acrylic, such as a shaded polymethylmethacrylate (PMMA), and may also secure artificial teeth (203, 204) within denture support regions of the monolithic support structure. The support body (307) of the monolithic support structure may be partially or fully encapsulated by the formable material (302), maintaining aperture openings, for example by use of a blocking material. The cervical region of teeth projections (301, 301') and artificial teeth (303, 303', 304) encapsulated by the formable material, are thus, subgingivally located in the implant-supported dental device. The crown regions of teeth projections are exposed extending beyond the formable material.

Artificial teeth for use in the implant-supported dental device may comprise commercially available artificial teeth, such as denture teeth sold under the trade names, Kenson and Vita, handmade teeth, and the like. Known denture teeth made of a material such as acrylic, or PMMA, or an acrylic composite are provided in a wide variety of sizes, shapes, and shades. In one embodiment, artificial teeth are selected from a digital teeth library of a denture design software program when digitally designing the monolithic support structure, ensuring appropriate spacing of the artificial teeth in the implant-supported dental device.

In one embodiment, an implant-supported dental device comprises artificial teeth that comprise a first material having different material properties than a second material used to form the monolithic support structure. In a specific embodiment, the monolithic support structure comprises a material having higher wear resistance, flexural strength and/or fracture toughness values than the material of the artificial teeth, and or the gingiva region. In one embodiment, the monolithic support structure comprises a ceramic material having a flexural strength value greater than about 650 MPa, or greater than about 800 MPa, when tested in accordance with ISO-6872:2008, which is greater than the flexural strength of the material used to form the artificial teeth.

Disadvantageously, denture teeth made of soft material are prone to wear and breakage in traditional dentures during normal use by a patient. Artificial teeth present over the entire arch, or in specific anterior or posterior locations, for example, may break or wear from contact or bite force during biting, chewing, and/or occlusion. In one embodiment, artificial teeth may be protected from wear for example, in lateral excursion, by placement of teeth projections that bears the forces of normal wear. While not wishing to be bound by theory, the material properties of the monolithic support structure may protect artificial teeth from chipping, wear, breakage and/or loosening of the artificial teeth, in some embodiments by distributing contact and bite force predominantly on or between teeth projections and/or natural dentition.

A method is also provided for making the implant-supported dental device. In one method, a method comprises forming a dental device wax set-up comprising a sintered ceramic monolithic support structure that comprises teeth projections and artificial teeth support regions between the teeth projections. The method further comprises obtaining artificial teeth, setting the artificial teeth in wax in the artificial tooth support regions of the monolithic support structure, and forming a wax gingiva. Optionally, inserts may by placed into cylinder guides on the monolithic support structure.

The method may further comprise forming a mold of the wax set-up for casting the final implant-supported dental device. Traditional mold-forming techniques and materials known in the dental industry may be used to make a mold of the set-up. By way of example, and not be limitation, mold making materials include sodium alginate, rubber, stone, hydrocolloid, polyether and silicones including condensation cured silicones and addition-cured silicones, including polyvinyl siloxane (PVS). The set-up may be pressed to form a mold. Alternately, the set-up may be placed in a secondary container and a liquid formable material may be poured around the set-up. Replicas or block-out material may be placed in the apertures to prevent impression material from blocking the holes.

The method further comprises placing the wax set-up in the mold, and removing the wax, for example, by melting and pouring it out, leaving the artificial teeth and monolithic support structure in position within the model. A formable material suitable for forming the actual gingival portion of a denture, such as acrylic, may be poured, injected or packed into the mold. Upon solidification, an implant-supported dental device comprising a monolithic support structure, artificial gingiva and artificial teeth that are held in place by the acrylic, is formed.

A method is provided for designing the monolithic support structure. In one embodiment a method is provided that comprises obtaining digital patient specific information of a patient's oral anatomy and implant information of an implant implanted in the patient's jaw; forming a digital model of the patient's oral anatomy from the patient specific information; creating a digital design comprising a digital support structure comprising digital teeth and apertures, based on the digital model of the patient specific information and implant information; forming digital instructions readable by an automated manufacturing machine to make the digital design; and utilizing the digital instructions in an automated manufacturing process to make a monolithic support structure.

A computer-implemented method is provided for making the digital model of the monolithic support structure from patient specific information. One or more electronic images capturing a patient's oral situation is obtained as digital data, and may comprise information about a patient's edentulous ridge or soft tissue in need of dental restoration, surrounding dentition, opposing dentition, occlusal relationship between jaws, and implant position for implants implanted in the jaw of a patient. Optionally, the digital data may be captured as images from direct intraoral scanning of a patient's anatomy, for example, obtained by a dentist using commercially available intraoral scanners.

Scans may also be obtained from physical impressions taken by traditional dental methods using trays and commercially available dental impression materials. Electronic images may also be obtained for example, by scanning models of a patient's anatomy, for example with a table-top or box scanner commercially available for use with dental applications. Physical models can be made from a cast of an impression, for example in stone, plaster or polymeric material. A temporary, try-in, or permanent denture previously made for a patient may also be used as a model to obtain patient specific information. A plurality of scans may be merged into a digital model of the restoration jaw, and optionally, the opposing dentition or jaw.

Computer-implemented systems suitable for designing the monolithic support structure, and optionally, also the implant-supported device, include commercially available CAD systems having dental design computer programs for designing patient-specific, implant-supported denture devices, bars and bridges, and/or full mouth contour restorations. Dental design systems, such as those sold under the trade name 3Shape, may be suitable for use herein. Other method, processes or systems, that may be used in whole or in part, are described in commonly owned U.S. patent application Ser. Nos. 14/142,382; 14/142,393; and 14/200,689, which are hereby incorporated in their entirety.

Digital teeth arrangements may be obtained, for example, by scanning existing dentures or wax set-ups. Alternatively, digital teeth arrangements may be designed based on the digital model of the patient's oral situation. Digital teeth may be selected from a digital tooth library having a size and shape compatible with any natural remaining dentition. Digital teeth are aligned to the patient's digital model, the position of implants and any surrounding or opposing dentition.

A digital support structure is designed in supporting arrangement with the digital teeth design, and also has a shape corresponding to the contour of a portion of the digital model of the patient's jaw in need of restoration. Digital apertures are designed on the support bar that align with the position and orientation of the implants.

In one embodiment, an entire set of teeth is digitally arranged on the digital support bar, and the digital teeth design is merged with the digital support bar. Subsequently, a portion of the digital teeth are removed leaving only digital teeth that correspond with teeth projections merged onto the support bar. A digital monolithic support structure is created that comprise the support bar and merged teeth from which instructions may be created to be used by an automated manufacturing machine.

In another embodiment, a digital support structure is digitally designed, and one or more digital teeth are selected and aligned on the digital support bar. The selected digital teeth correspond to teeth projections on the final monolithic support structure. The digital teeth are arranged on the digital support structure and merged with the support structure to form a digital monolithic support structure.

The digital teeth design and the digital support structure design may comprise one or more digital files, and where necessary merged as a single digital design file. The merged file of the digital teeth arrangement design and the digital support structure may be converted into output files, and/or instructions for use in automated manufacturing processes. Files of the digital support structure comprising digital teeth in the form of one or more instruction file(s) may be sent to a rapid manufacturing machine, such as a mill, to produce the monolithic structure.

As will be apparent, the features and attributes of the specific embodiments disclosed herein may be combined in different ways to form additional embodiments that fall within the scope of the present disclosure. Alternate implementations of processes are included within the scope of the embodiments described herein in which elements and functions may, for example, be deleted or executed out of the order disclosed. Method and process steps for the digital designs disclosed, may be embodied in software code modules executed by one or more general purpose computers or processors, such as those known for use in dental design and automated manufacturing processes. Although this invention has been disclosed in context of certain specific embodiments, it will be understood by those skilled in the art, for example, that the present invention extends beyond the specific disclosure to include obvious equivalence, modifications or alternate uses.

We claim:

1. A method of making a monolithic support structure for use in an implant-supported denture device comprising the steps of:
    obtaining digital patient specific information of a patient's oral anatomy and implant information of an implant implanted in the patient's jaw;
    forming a digital model of the patient's oral anatomy including a portion of the patient's edentulous ridge to be restored and the implant from the patient specific information;
    creating a digital design for a monolithic support structure comprising,
        designing a digital support structure comprising a support body having an elongated portion comprising an attachment side oriented adjacent the portion of the edentulous ridge, and a crown side that is opposite the attachment side,
        aligning a plurality of digital teeth with the edentulous ridge,
        merging at least a portion of the digital teeth at a cervical region with the crown side of the support body, and
        forming the digital support structure wherein the crown side of the support body comprises at least one digital tooth projecting therefrom and at least one digital edentulous region adjacent at least one digital tooth,
    forming digital instructions readable by an automated manufacturing machine that correspond to the digital design for the monolithic support structure; and
    utilizing the digital instructions in an automated manufacturing process to make a monolithic support structure comprising, as a single, unitary body of material, a support body comprising a crown side, one or more teeth projections extending from the crown side of the support body and at least one artificial tooth support region on the crown side adjacent the teeth projections that corresponds to the digital edentulous region.

2. The method of claim 1, wherein the automated manufacturing process comprises a milling process.

3. The method of claim 2, comprising milling the monolithic support structure from a monolithic block of ceramic material.

4. The method of claim 1, wherein the automated manufacturing process comprises an additive manufacturing process to make the monolithic support structure as a unitary body.

5. The method of claim 1, wherein the digital teeth are selected from a digital tooth library.

6. The method of claim 1, wherein the digital teeth have a size and shape of fully formed restoration teeth.

7. The method of claim 1 further comprising the step of removing one or more of the plurality of digital teeth to form the digital edentulous region.

8. A method of making a monolithic support structure that may be incorporated into an implant-supported dental device, comprising the steps of:
    obtaining digital instructions, readable by an automated manufacturing machine, that correspond to a digital design of a support structure comprising teeth and apertures that is specific to a patient's oral anatomy and implant information of an implant implanted in the patient's jaw; and
    utilizing the digital instructions to shape a monolithic support structure in the automated manufacturing process, wherein the monolithic support structure comprises
        a support body having an elongated portion comprising an attachment side and a crown side that is opposite the attachment side,
        one or more teeth projections extending from the crown side of the support body,
        one or more apertures through the thickness of the monolithic support body, and
        at least one region providing a framework to position a discrete artificial tooth adjacent the crown side of the support body and adjacent at least one of the teeth projections.

9. The method of claim 8, wherein the automated manufacturing process comprises milling the monolithic support structure from a single ceramic block.

10. The method of claim 9, wherein the ceramic block is comprises a partially sintered zirconia ceramic body and the process comprises milling the ceramic block into the monolithic support structure to a scaled factor based on a predicted size reduction upon sintering.

11. The method of claim 9, further comprising sintering the monolithic support structure to form a sintered ceramic monolithic support structure.

12. The method of claim 11, further comprising forming an implant-supported denture device by incorporating a plurality of discrete artificial teeth within the framework adjacent the crown side of the support body and the one or more sintered ceramic tooth projections, and forming an artificial gingival region with a formable material, holding the plurality of discrete artificial teeth within the framework, and surrounding the support body and a cervical region of the one or more sintered ceramic tooth projections with the formable material.

13. The method of claim 12, wherein the sintered ceramic monolithic support structure comprises teeth projections consisting essentially of sintered zirconia ceramic, and the discrete artificial teeth and the artificial gingival region comprise acrylic.

14. The method of claim 8, further comprising sintering the monolithic support structure and forming a fully sintered ceramic monolithic support structure wherein the one or more tooth projections comprise fully contoured dental restorations having crown regions with anatomical features consistent with the tooth type to be restored.

* * * * *

UNITED STATES PATENT AND TRADEMARK OFFICE
CERTIFICATE OF CORRECTION

| | | |
|---|---|---|
| PATENT NO. | : 9,649,180 B2 | Page 1 of 1 |
| APPLICATION NO. | : 14/709752 | |
| DATED | : May 16, 2017 | |
| INVENTOR(S) | : David Morales and Nhung Tieu Truong | |

It is certified that error appears in the above-identified patent and that said Letters Patent is hereby corrected as shown below:

In the Specification

Column 9, Line 14: the text "may by placed" should read --may be placed--
Column 9, Line 20: the text "not be limitation" should read --not by limitation--
Column 12, Lines 33-34: the text "block is comprises a partially" should read --block comprises a partially--

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*